(12) United States Patent
Cheng et al.

(10) Patent No.: US 10,118,909 B2
(45) Date of Patent: Nov. 6, 2018

(54) MONASCUSPURPURONES, PREPARATION AND USES THEREOF

(71) Applicant: Food Industry Research and Development Institute, Hsinchu (TW)

(72) Inventors: Ming-Jen Cheng, Hsinchu (TW);
Ping-Hsun Yang, Hsinchu (TW);
Ming-Der Wu, Hsinchu (TW);
Shie-Jea Lin, Hsinchu (TW);
Gwo-Fang Yuan, Hsinchu (TW);
Yen-Lin Chen, Hsinchu (TW);
Hsuen-Chun Liao, Hsinchu (TW);
Kai-Ping Chen, Hsinchu (TW)

(*) Notice: Subject to any disclaimer, the term of this patent is extended or adjusted under 35 U.S.C. 154(b) by 102 days.

(21) Appl. No.: 14/511,136

(22) Filed: Oct. 9, 2014

(65) Prior Publication Data

US 2015/0139978 A1 May 21, 2015

Related U.S. Application Data

(63) Continuation of application No. 13/336,234, filed on Dec. 23, 2011.

(60) Provisional application No. 61/426,801, filed on Dec. 23, 2010.

(51) Int. Cl.
| | | |
|---|---|---|
| A01N 65/04 | (2009.01) | |
| C07D 307/86 | (2006.01) | |
| A61K 31/365 | (2006.01) | |
| A61K 31/426 | (2006.01) | |
| A61K 31/455 | (2006.01) | |
| A61K 45/06 | (2006.01) | |
| C12P 17/04 | (2006.01) | |
| C12R 1/645 | (2006.01) | |
| A61K 36/899 | (2006.01) | |
| B01D 15/18 | (2006.01) | |
| B01D 15/42 | (2006.01) | |

(52) U.S. Cl.
CPC .......... *C07D 307/86* (2013.01); *A61K 31/365* (2013.01); *A61K 31/426* (2013.01); *A61K 31/455* (2013.01); *A61K 36/899* (2013.01); *A61K 45/06* (2013.01); *B01D 15/18* (2013.01); *B01D 15/424* (2013.01); *C12P 17/04* (2013.01); *C12R 1/645* (2013.01); *A61K 2236/19* (2013.01)

(58) Field of Classification Search
CPC .............. A61K 2300/00; A61K 31/365; A61K 31/426; A61K 31/455; A61K 4436/19; A61K 36/899; A61K 45/06; B01D 15/18; B01D 15/424; C07D 307/86; C12P 17/04; C12R 1/645; A24F 47/006
See application file for complete search history.

(56) References Cited

U.S. PATENT DOCUMENTS

| | | | | |
|---|---|---|---|---|
| 6,046,022 A | * | 4/2000 | Zhang | A61K 36/062 424/255.1 |
| 2008/0261913 A1 | * | 10/2008 | Sommadossi | C07F 9/65586 514/47 |
| 2009/0318501 A1 | * | 12/2009 | Baldwin | C07D 405/12 514/326 |

OTHER PUBLICATIONS

Jeon et al. Life Sci. (2004) 75: 3195-3203.*
Chen et al. Int. J. Obesity (2008) 32: 1694-1704.*
Cheng et al. Helvetica Chimica Acta (2011) 94(9): 1638-1605.*

* cited by examiner

*Primary Examiner* — Susan Marie Hanley
(74) *Attorney, Agent, or Firm* — WPAT, P.C., Intellectual Property Attorneys; Anthony King

(57) ABSTRACT

The present invention relates to a monascuspurpurone compound of formula (I):

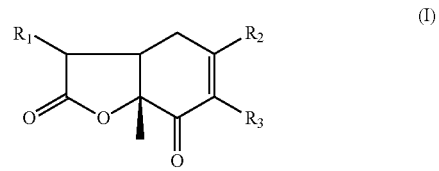

or a pharmaceutically acceptable derivative thereof as described in the specification, the process for preparation of the same, and the composition comprising the same. The uses of a monascuspurpurone compound for promoting adipocyte differentiation, for increasing the activity of PPARγ and/or C/EBPα, for lowering blood glucose, for preventing and/or treating a disease or disorder related to insulin resistance, and for preventing and/or treating metabolic syndrome or its complications are also provided.

7 Claims, 6 Drawing Sheets

(A) Insulin (B) 2 μg/ml (C) 5 μg/ml (D) 10 μg/ml

MONASCUSPURPURONES, PREPARATION AND USES THEREOF

CROSS REFERENCE TO RELATED APPLICATIONS

This application is a Continuation of U.S. application Ser. No. 13/336,234, filed on Dec. 23, 2011, which claims priority to U.S. Provisional Application No.: 61/426,801, filed on 23 Dec. 2010.

FIELD OF THE INVENTION

This invention relates to novel monascuspurpurones and the process for preparation of the same. It further relates to the compositions comprising a monascuspurpurone compound, and the uses of a monascuspurpurone compound for promoting adipocyte differentiation, for increasing the activity of PPARγ and/or C/EBPα, for lowering blood glucose, and for preventing and/or treating a disease or disorder related to insulin resistance, such as metabolic syndrome. The invention also relates to the use of extracts of red yeast-fermented products for preventing and/or treating a disease or disorder related to insulin resistance, such as metabolic syndrome.

BACKGROUND OF THE INVENTION

*Monascus* has been used in Chinese fermented foods for thousands of years. Various pharmaceutical uses of *Monascus* fermented products have also been recorded. In addition to traditional use in production of pigments, red yeast rice fermented with *Monascus* spp. has recently been used to produce bioactive metabolites such as γ-aminobutyric acid (GABA) used as an anti-hypertension agent (see Tsuji, K., et al., 1992, "Effects of two kinds of Koji on blood pressure in spontaneously hypertensive rats." *Nippon. Nogeikagaku Kaishi.*, 66: 1241-1246), polyketides monacolin K used as a cholesterol-lowering drug (see Endo, A., 1979, "Monacolin K, a new hypocholesterolemic agent produced by a *Monascus* species." *J. Antbiot.*, 32: 852-854; Endo, A., 1985, "Compactin (ML-236B) and related compounds as potential cholesterol-lowering agents that inhibit HMG-CoA reductase." *J. Med. Chem.*, 28: 401-405; and Martinokova, L., et al., 1995, "Biological activity of polyketide pigments produced by the fungus *Monascus.*" *J. Appl. Bacteriol.*, 79: 609-616), and demerumic acid used as an anti-oxidant (see Juzlová, P., et al., 1996, "Secondary Metabolites of the Fungus *Monascus*: a Review." *Journal of Industrial Microbiology*, 16: 163-170). Furthermore, red yeast rice fermented with *Monascus* spp. has been reported to inhibit tumor growth, protect liver function, inhibit adipocyte differentiation, resist fatigue, improve immune function, lower hyperlipidemia, and lower blood glucose, and is widely consumed as a health food and drug (see Loret, M.-O. & Morel, S., 2010, "Isolation and structural characterization of two new metabolites from *Monascus.*" *J Agric Food Chem.*, 58: 1800-1803).

A randomized double-blind controlled trial conducted in the University of California, Los Angeles Medical Center (see Heber D., et al., 1999, "Cholesterol-lowering effects of a proprietary Chinese red-yeastrice dietary supplement." *Am J Clin Nutr.*, 69: 231-236) found that LDL, total cholesterol, and triglycerides in subjects suffering from hyperlipidemia decreased by 22%, 17%, and 11%, respectively, in the experimental group treated with the red yeast rice fermented with *Monascus* spp., while those in the control group maintained the original values. The study also confirmed that red yeast rice fermented with *Monascus* spp. is superior to conventional lipid-lowering drugs because it does not adversely affect liver function or cause other side effects. According to a report by the Shanghai First People's Hospital regarding the effect of red yeast rice fermented with *Monascus* spp. as compared with Pravastatin in treating hyperlipidemia (see Yang H T., et al., 1997, "A comparative Study of Xuezhikang and Mevalotin in treatment of Essential Hyperlipidemia." *Chinese Journal of New Drugs*, 6: 265-268), total cholesterol, low density lipoprotein cholesterol and Apo B decreased by 26.59% vs 18.92%, 33.32% vs 24.24%, and 18.42% vs 8.89%, respectively, showing that the red yeast rice fermented with *Monascus* spp. has a significantly superior effect. A study conducted at the Chinese Academy of Medical Sciences Deng Sisuo Hospital (see Lin, Feng., 1992, "Evolution of research and development of *Monascus.*" *Scientific agriculture*, 40: 193-198) also confirmed that red yeast rice fermented with *Monascus* spp. is effective in treatment of subjects with high cholesterol. Red yeast rice fermented with *Monascus* spp. has since become commercialized as a lipid-lowering drug and for prevention of coronary heart disease.

In addition, the blood-glucose-lowering effect of red yeast rice fermented with *Monascus* spp. was reported in 1988 (see Tamada Hideaki, 1988, "Red yeast rice application of a variety of seasonings." Food and Science, July: 96-99). The blood glucose level of rabbits fed red yeast rice fermented with *Monascus* spp. was reduced by about 30%. Shi, Y. and Pan, T., J. ("Anti-diabetic effects of *Monascus purpureus* NTU 568 fermented products on streptozotocin-induced diabetic rats." *J. Agric. Food Chem.*, 2010, 58(13): 7634-7640) report that red yeast rice fermented with *Monascus* spp. has anti-diabetic effects.

Modulating lipid metabolism is one strategy for the treatment of metabolic syndrome. Thiazolidinediones (TZDs) are type 2 diabetes drugs developed in the early 1980s. Studies on the mechanisms of TZDs showed that they increase insulin sensitivity by activating PPARγ. One of the characteristic effects of activating PPARγ is increasing differentiation of adipocytes. Increasing adipocyte differentiation has therefore become a popular method for screening agents that have potential in activating PPARγ and decreasing insulin resistance.

However, the prior arts do not disclose which compounds in the red yeast rice fermented with *Monascus* spp. have the anti-diabetic effects and what their pharmacological mechanism is.

SUMMARY OF THE INVENTION

One purpose of the invention is to provide a compound of formula (I):

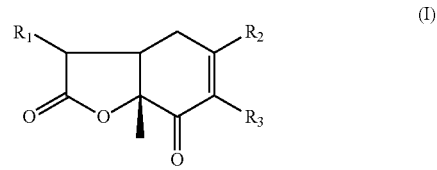

or a pharmaceutically acceptable derivative thereof,
wherein $R^1$ and $R^2$ are independently selected from the group consisting of alkyl, alkenyl, and carbonyl, and $R^3$ is alkyl.

Another purpose of the present invention is to provide a composition comprising the compound of formula (I) or a pharmaceutically acceptable derivative thereof, and optionally a pharmaceutically acceptable carrier or excipient.

Another purpose of the present invention is to provide a process for the preparation of the compound of formula (I) or a pharmaceutically acceptable derivative thereof.

Another purpose of the present invention is to provide a red yeast rice extract.

Another purpose of the present invention is to provide a composition comprising the red yeast rice extract of the invention, and optionally a pharmaceutically acceptable carrier or excipient.

Another purpose of the present invention is to provide a method for promoting adipocyte differentiation in a subject.

Another purpose of the present invention is to provide a method for increasing the activity of PPARγ and/or C/EBPα.

Another purpose of the present invention is to provide a method of preventing and/or treating a disease or disorder related to insulin resistance in a subject.

Another purpose of the present invention is to provide a method of lowering blood glucose in a subject.

Still another purpose of the present invention is to provide a method of preventing and/or treating metabolic syndrome or its complications.

The present invention is described in detail in the following sections. Other characteristics, purposes and advantages of the present invention can be easily found in the detailed description and claims.

DETAILED DESCRIPTION OF THE INVENTION

Figure 1:
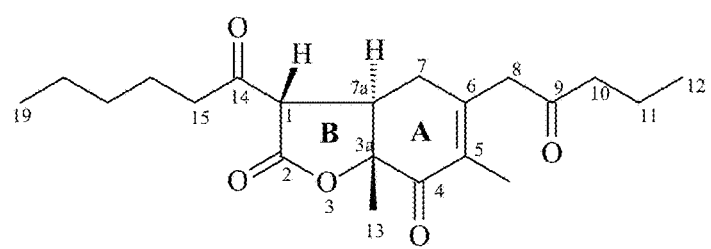
FIG. 1 shows the structure of rel-(1S,7aR,3aR)-1-Hexanoyl-5,13-dimethyl-6-(2-oxopentyl)-7a,7-dihydrobenzofuran-2,4-dione (Compound 1).

The present invention can be more readily understood by reference to the following detailed description of various embodiments of the invention, the examples, and the chemical drawings and tables with their relevant descriptions. It is to be understood that unless otherwise specifically indicated by the claims, the invention is not limited to specific preparation methods, carriers or formulations, or to particular modes of formulating the compounds of the invention into products or compositions intended for topical, oral or parenteral administration, because as one of ordinary skill in the relevant arts is well aware, such things can, of course, vary. It is also to be understood that the terminology used herein is for the purpose of describing particular embodiments only and is not intended to be limiting.

Definitions

As utilized in accordance with the present disclosure, the following terms, unless otherwise indicated, shall be understood to have the following meaning:

As used herein, the term "alkyl" and "alkenyl" include straight and branched chains.

"Alkyl" refers to a hydrocarbon group that can be conceptually formed from an alkane by removing hydrogen from the structure of a non-cyclic hydrocarbon compound having straight or branched carbon chains, and replacing the hydrogen atom with another atom or organic or inorganic substituent group. In some embodiments of the invention, the alkyl groups are "$C_1$ to $C_{10}$ alkyl" such as methyl, ethyl, propyl, isopropyl, n-butyl, iso-butyl, sec-butyl, tert-butyl, amyl, tert-amyl, hexyl and the like. Many embodiments of the invention comprise "$C_1$ to $C_7$ alkyl" groups that include methyl, ethyl, propyl, iso-propyl n-butyl, iso-butyl, sec-butyl, t-butyl, pentyl, hexyl, and heptyl groups.

The term "alkenyl" is structurally analogous to an alkyl group or residue that comprises at least one carbon-carbon double bond. In some embodiments, the alkenyl groups are "$C_2$ to $C_7$ alkenyls" which are exemplified by vinyl, allyl, propenyl, 2-butenyl, 3-butenyl, 2-pentenyl, 3-pentenyl, 4-pentenyl, 2-hexenyl, 3-hexenyl, 4-hexenyl, 5-hexenyl, 2-heptenyl, 3-heptenyl, 4-heptenyl, 5-heptenyl, and 6-heptenyl, as well as dienes and trienes of straight and branched chains. In other embodiments, alkenyls are limited to two to four carbon atoms.

As used herein, the term "carbonyl" includes straight and branched chains.

"Carbonyl" refers to a functional group comprising a carbon atom double-bonded to an oxygen atom: C=O. In some embodiments of the invention, the carbonyl group is "$C_1$ to $C_{10}$ carbonyl."

The term "a pharmaceutically acceptable derivative" or "pharmaceutically acceptable derivatives" as used herein denotes a compound that is modified from the compound of the invention but that has properties and efficacies that are the same as or better than those of the compound of the invention. Preferably, the pharmaceutically acceptable derivative is a pharmaceutically acceptable salt, solvate, hydrate, or prodrug of the compound of the invention.

One or more of the compounds of the invention may be present as a salt. The term "salt" encompasses those salts formed with the organic and inorganic anions and cations. Furthermore, the term includes salts that form by standard acid-base reactions with basic groups and organic or inorganic acids. Such acids include hydrochloric, hydrofluoric, trifluoroacetic, sulfuric, phosphoric, acetic, succinic, citric, lactic, maleic, fumaric, palmitic, cholic, pamoic, mucic, D-glutamic, D-camphoric, glutaric, phthalic, tartaric, lauric, stearic, salicyclic, methanesulfonic, benzenesulfonic, sorbic, picric, benzoic, and cinnamic acids.

The compounds of the invention can also exist as solvates and hydrates. Thus, these compounds may crystallize with, for example, waters of hydration, or one, a number of, or any fraction of molecules of the mother liquor solvent. The solvates and hydrates of such compounds are included within the scope of this invention.

The term "subject" as used herein denotes any animal, preferably a mammal, and more preferably a human. Examples of subjects include humans, non-human primates, rodents, guinea pigs, rabbits, sheep, pigs, goats, cows, horses, dogs and cats.

The term "effective amount" of a compound as provided herein means a sufficient amount of the compound to provide the desired regulation of a desired function, such as gene expression, protein function, or the induction of a particular type of response. As will be pointed out below, the exact amount required will vary from subject to subject, depending on the disease state, physical conditions, age, sex, species and weight of the subject, the specific identity and formulation of the composition, etc. Dosage regimens may be adjusted to induce the optimum therapeutic response. For example, several divided doses may be administered daily or the dose may be proportionally reduced as indicated by the exigencies of the therapeutic situation. Thus, it is not possible to specify an exact "effective amount." However, an appropriate effective amount can be determined by one of ordinary skill in the art using only routine experimentation.

The term "preventing" or "prevention" is recognized in the art, and when used in relation to a condition, it includes administering, prior to onset of the condition, an agent to reduce the frequency or severity of or delay the onset of symptoms of a medical condition in a subject relative to a subject which does not receive the agent.

The term "treating" or "treatment" as used herein denotes reversing, alleviating, inhibiting the progress of, or improving the disorder or condition to which such term applies, or one or more symptoms of such disorder or condition.

The term "carrier" or "excipient" as used herein refers to any substance, not itself a therapeutic agent, used as a carrier and/or diluent and/or adjuvant, or vehicle for delivery of a therapeutic agent to a subject or added to a formulation to improve its handling or storage properties or to permit or facilitate formation of a dose unit of the composition into a discrete article such as a capsule or tablet suitable for oral administration. Suitable carriers or excipients are well known to persons of ordinary skill in the art of manufacturing pharmaceutical formulations or food products. Carriers or excipients can include, by way of illustration and not limitation, buffers, diluents, disintegrants, binding agents, adhesives, wetting agents, polymers, lubricants, glidants, substances added to mask or counteract a disagreeable taste or odor, flavors, dyes, fragrances, and substances added to improve appearance of the composition. Acceptable carriers or excipients include citrate buffer, phosphate buffer, acetate buffer, bicarbonate buffer, stearic acid, magnesium stearate, magnesium oxide, sodium and calcium salts of phosphoric and sulfuric acids, magnesium carbonate, talc, gelatin, acacia gum, sodium alginate, pectin, dextrin, mannitol, sorbitol, lactose, sucrose, starches, gelatin, cellulosic materials (such as cellulose esters of alkanoic acids and cellulose alkyl esters), low melting wax cocoa butter, amino acids, urea, alcohols, ascorbic acid, phospholipids, proteins (for example, serum albumin), ethylenediamine tetraacetic acid (EDTA), dimethyl sulfoxide (DMSO), sodium chloride or other salts, liposomes, mannitol, sorbitol, glycerol or powder, polymers (such as polyvinyl-pyrrolidone, polyvinyl alcohol, and polyethylene glycols), and other pharmaceutically acceptable materials. The carrier should not destroy the pharmacological activity of the therapeutic agent and should be non-toxic when administered in doses sufficient to deliver a therapeutic amount of the agent.

Often, ranges are expressed herein as from "about" one particular value and/or to "about" another particular value. When such a range is expressed, an embodiment includes the range from the one particular value and/or to the other particular value. Similarly, when values are expressed as approximations, by use of the word "about," it will be understood that the particular value forms another embodiment. It will be further understood that the endpoints of each of the ranges are significant both in relation to and independently of the other endpoint.

"Optional" or "optionally" means that the subsequently described event or circumstance may or may not occur, and that the description includes instances where said event or circumstance occurs and instances where it does not. For example, the phrase "optionally comprise an agent" means that the agent may or may not exist.

It must be noted that, as used in the specification and the appended claims, the singular forms "a," "an" and "the" include plural referents unless the context clearly dictates otherwise. Thus, unless otherwise required by context, singular terms shall include the plural and plural terms shall include the singular.

The Compounds of the Invention

The present invention relates to a prupurone or a pharmaceutically acceptable derivative thereof. The monascuspurpurone of the invention has the following formula (I):

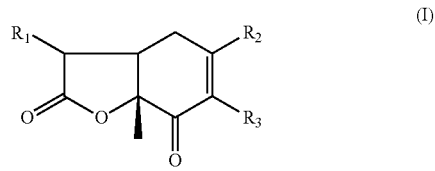

wherein $R^1$ and $R^2$ are independently selected from the group consisting of alkyl, alkenyl, and carbonyl, and $R^3$ is alkyl.

In some preferred embodiments of the compound of formula (I), $R^1$ and $R^2$ are independently $C_1$-$C_{10}$ alkyl, $C_2$-$C_7$ alkenyl or $C_1$-$C_{10}$ carbonyl. More preferably, $R^1$ is hexanoyl. In another aspect, $R^2$ is more preferably 2-oxopentyl.

In some preferred embodiments of the compound of formula (I), $R^3$ is $C_1$-$C_{10}$ alkyl. More preferably, $R^3$ is methyl.

In a most preferred embodiment, the compound of formula (I) is rel-(1S,7aR,3aR)-1-hexanoyl-5,13-dimethyl-6-(2-oxopentyl)-7a,7-dihydrobenzofuran-2,4-dione.

The compounds of the invention are preferably further converted into a pharmaceutically acceptable derivative, such as a pharmaceutically acceptable salt, solvate or prodrug, by any known methods.

The Compositions of the Invention

The present invention also provides a composition comprising the compound of the invention or a pharmaceutically acceptable derivative thereof. The composition of the invention is preferably a food composition or a pharmaceutical composition. The compound of formula (I) of the present invention in the composition is preferably provided in the form of an extract of red yeast rice or a chemical compound.

The pharmaceutical composition of the invention is preferably administered topically or systemically by any method known in the art, including, but not limited to, intramuscular, intradermal, intravenous, subcutaneous, intraperitoneal, intranasal, oral, mucosal or external routes. The appropriate route, formulation and administration schedule can be determined by those skilled in the art. In the present invention, the pharmaceutical composition can be formulated in various ways, according to the corresponding route of administration, such as a liquid solution, a suspension, an emulsion, a syrup, a tablet, a pill, a capsule, a sustained release formulation, a powder, a granule, an ampoule, an injection, an infusion, a kit, an ointment, a lotion, a liniment, a cream or a combination thereof. If necessary, it may be sterilized or mixed with any pharmaceutically acceptable carrier or excipient, many of which are known to one of ordinary skill in the art.

The Preparation Processes of the Invention

The present invention provides a process for the preparation of the compound of formula (I):

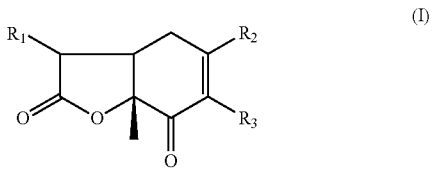

or a pharmaceutically acceptable derivative thereof,
wherein $R^1$ and $R^2$ are independently selected from the group consisting of alkyl, alkenyl, and carbonyl, and $R^3$ is alkyl.

In one preferred embodiment, the process of the invention comprises the steps of:
(a) fermenting rice with the isolated strain of *Monascus* spp. to obtain red yeast rice;
(b) extracting the dried red yeast rice with methanol, ethanol or ethyl acetate;
(c) extracting the extract obtained in step (b) between ethyl acetate and $H_2O$ to obtain an ethyl acetate-soluble fraction;
(d) eluting the ethyl acetate-soluble fraction through a silica gel chromatographic column with eluents; and
(e) purifying the eluted fraction of (d) with silica gel chromatographic column and/or preparative thin layer chromatography (TLC) to obtain the compound.

According to the process of the invention, the isolated strain can be *Monascus pilosus*, *Monascus purpureus*, or *Monascus ruber*, preferably *Monascus purpureus*; more preferably *Monascus purpureus* M615 (DSM 24162).

According to the process of the invention, prior to step (b), the red yeast rice is preferably dried.

According to the process of the invention, step (a) preferably comprises fermenting rice with an isolated strain of *Monascus* spp. in the presence of tartaric acid to obtain red yeast rice.

According to the process of the invention, the ratio of ethyl acetate and $H_2O$ in step (c) is preferably about 1:1.

According to the process of the invention, step (d) preferably comprises loading the ethyl acetate-soluble fraction into a chromatographic column with silica gel and eluting the column with an eluent comprising n-hexane/ethyl acetate 10:1 to 5:1 to produce fifteen fractions. The eluted fraction used in step (e) is Fraction 10.

According to a preferred process of the invention, step (e) uses TLC with n-hexane/EtOAc, 5:1 as solvent.

The present invention provides processes for the preparation of red yeast rice extracts. In one preferred embodiment, the process comprises the steps of:
(a) fermenting rice with an isolated strain of *Monascus* spp. to obtain red yeast rice; and
(b) extracting the red yeast rice with methanol, ethanol or ethyl acetate.

According to the red yeast rice extract preparation process of the invention, the isolated strain can be *Monascus pilosus*, *Monascus purpureus*, or *Monascus ruber*, preferably *Monascus purpureus*, more preferably *Monascus purpureus* M615 (DSM 24162).

According to the red yeast rice extract preparation process of the invention, prior to step (b), the red yeast rice is preferably dried.

Utilities

One aspect of the therapeutic method of the present invention is to promote adipocyte differentiation in a needed subject, which comprises administering to said subject an effective amount of a compound of formula (I)

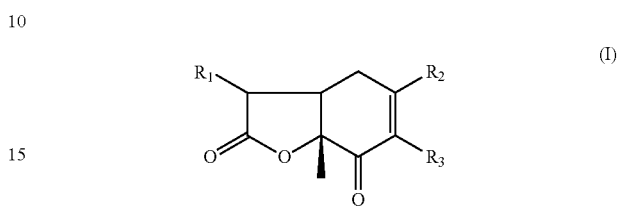

or a pharmaceutically acceptable derivative thereof,
wherein $R^1$ and $R^2$ are independently selected from the group consisting of alkyl, alkenyl, and carbonyl, and $R^3$ is alkyl;
or a red yeast rice extract.

Another aspect of the therapeutic method of the present invention is to increase the activity of PPARγ and/or C/EBPα. Preferably, the compound of formula (I) or a pharmaceutically acceptable derivative thereof, or a red yeast rice extract promotes adipocyte differentiation through the PPARγ/C/EBPα pathway.

Another aspect of the therapeutic method of the present invention is to lower blood glucose in a subject, which comprises administering to said subject an effective amount of the compound of formula (I) or a pharmaceutically acceptable derivative thereof, or a red yeast rice extract.

Another aspect of the therapeutic method of the present invention is to prevent and/or treat a disease or disorder related to insulin resistance in a subject, which comprises administering to said subject an effective amount of the compound of formula (I) or a pharmaceutically acceptable derivative thereof, or a red yeast rice extract.

In certain embodiments, the disease or disorder related to insulin resistance is metabolic syndrome or its complications, such as atherogenic dyslipidemia, elevated blood pressure, insulin resistance or glucose intolerance, type 2 diabetes or cardiovascular disease.

According to the methods of the present invention, the compound of formula (I) or a pharmaceutically acceptable derivative thereof is preferably administered topically or systemically by any method known in the art, including, but not limited to, intramuscular, intradermal, intravenous, subcutaneous, intraperitoneal, intranasal, oral, mucosal or external routes. The appropriate route, formulation and administration schedule is determined by those skilled in the art.

According to the methods of the present invention, the compounds of formula (I) or a pharmaceutically acceptable derivative thereof is preferably administered in combination with a second agent effective in preventing and/or treating metabolic syndrome or its complications, thereby improving the therapeutic effect of the compounds of the invention. Many agents are known in the art to be effective in preventing and/or treating metabolic syndrome or its complications. Examples of such agents include, but are not limited to, drugs to control cholesterol levels and lipids, such as statins, fibrates, or nicotinic acid; drugs to control high blood pressure, such as diuretics or angiotensin-converting enzyme (ACE) inhibitors; and drugs to control high blood sugar, such as metformin, insulin, sulfonylurea (SU), biguanide, α-glucosidase inhibitors, thiazolidinediones (TZDs) and the like.

The following examples are provided to aid those skilled in the art in practicing the present invention.

EXAMPLES

Microorganism

*Monascus purpureus* M615 was deposited with the Deutsche Sammlung von Mikroorganismen and Zellkulturen GmbH (DSMZ), Mascheroder Weg 1b, D38124, Braunschweig, Germany, DSMZ on 28 Oct. 2010 in accordance with the Budapest Treaty and assigned accession number DSM 24162. It was also deposited with the Bioresource Collection and Research Center (BCRC) of the Food Industry Research and Development Institute (FIRDI), 331 Shih-Pin Road, 300, Hsinchu, Taiwan, R.O.C., on 27 Oct. 2010 and assigned accession number BCRC 930146.

Example 1

Preparation of Yeast Material

*M. purpureus* M615 was inoculated on a Potato Dextrose Agar (PDA) (Difco, USA) plate and incubated at 30° C. for 7 days. The spores were washed out from the PDA plate using 6 ml of sterile water and 1 ml of the spore suspension was inoculated in a 250 ml Erlenmeyer flask containing GSP medium (which contains 7% of glycerol, 3% of flour, 1.2% of polypeptone, 3% of soybean powder, 0.1% of magnesium sulfate and 0.2% of sodium nitrate) and shaken and incubated at 30° C., 150 rpm for three days to obtain the yeast material stock.

Example 2

Solid Fermentation 75 ml of 0.2% tartaric acid solution was added to each of ten 450-ml wide-mouth glass bottles each containing 75 g of Zailai rice (long grain rice). The rice was soaked at 4° C. overnight. Then, the liquid was drained off and the rice was sterilized. An aliquot of 7.5 ml of the yeast material stock obtained as mentioned above was inoculated in each bottle and incubated at 25° C. for 14 days (at the 7th day of the incubation, 7.5 ml of GSP medium were added to the culture) to obtain red yeast rice.

Example 3

Extraction and Isolation of New Compound from Red Yeast Rice

The red yeast rice prepared above was dried and then extracted three times with 95% EtOH at room temperature. The ethanol syrup extract was partitioned between AcOEt/$H_2O$ (1:1) to afford AcOEt (2.5 g) and $H_2O$ (10.2 g) soluble fractions. The AcOEt-soluble fraction (Fr. A, 2.5 g) was chromatographed over silica gel (75 g $SiO_2$, 70-230 mesh), eluted with n-hexane and enriched with AcOEt to produce 15 fractions: Fr. A1-A15. Fr. A11 (1.2 g) was re-subjected to column chromatography (30 g $SiO_2$, 70-230 mesh; n-hexane/AcOEt 10:1→5:1) to furnish 10 subfractions: Fr.A11.1-A11.10. Fr.A11.8 (18 mg) was purified by prep. TLC ($SiO_2$; n-hexane/AcOEt 5:1) to give Compound 1 (1.3 mg).

Example 4

Characterization of Compound 1

Optical rotations were measured on a Jasco P-1020 digital polarimeter, UV spectra were obtained on a Jasco UV-240 spectrophotometer in MeOH, and IR spectra (KBr or neat) were taken on a Perkin-Elmer System 2000 FT-IR spectrometer. 1D ($^1$H, $^{13}$C, DEPT) and 2D (COSY, NOESY, HSQC, HMBC) NMR spectra using $CDCl_3$ as solvent were recorded on a Varian Unity Plus 400 (400 MHz for $^1$H NMR, 100 MHz for $^{13}$C NMR). Chemical shifts were internally referenced to the solvent signals in $CDCl_3$ ($^1$H, δ 7.26; $^{13}$C, δ 77.0) with TMS as the internal standard. High-resolution ESI-MS spectra on a Bruker Daltonics APEX II 30e spectrometer. Silica gel (70-230, 230-400 mesh) (Merck) was used for column chromatography, and silica gel 60 F-254 (Merck) was used for TLC and prep. TLC.

Compound 1 has the characteristics shown in Table 1.

TABLE 1

$^1$H- and $^{13}$C-NMR Data ($CDCl_3$, 600 and 150 MHz, resp.) of compounds 1. δ in ppm, J in Hz.

| | 1 | |
|---|---|---|
| | δ(C) | δ(H) |
| H—C(1) or C(1) | 54.8 | 3.46 (d, J = 12.8) |
| C(2) | 169.5 | — |
| H—C(3) | — | — |
| C(3a) | 83.2 | — |
| C(4) or $CH_2$(4) | 193.4 | — |
| C(5) or H—C(5) | 148.2 | — |
| Me(5) | 11.8 | — |
| C(6) | 131.9 | — |
| $CH_2$(7) or C(7) | 42.9 | 2.58 (dt, J = 18.0, 10.8, $H_{ax}$) |
| | | 2.99 (dt, J = 18.0, 4.4, $H_{eq}$) |
| H—C(7a) | 42.3 | 3.16 (ddd, J = 12.8, 10.8, 4.4) |
| $CH_2$(8) or C(8) | 48.4 | 3.25 (d, J = 17.0) |
| | | 3.65 (d, J = 17.0) |
| C(9) | 205.9 | — |
| $CH_2$(10) or C(10) | 45.3 | 2.57 (t, J = 7.6) |
| $CH_2$(11) or Me(11) | 17.3 | 1.57-1.67 (m) |
| Me(12) | 13.6 | 0.94 (t, J = 7.6) |
| Me(13) | 17.2 | 1.49 (s) |
| C(14) | 202.4 | — |
| $CH_2$(15) | 33.4 | 2.47 (t, J = 7.6) |
| $CH_2$(16) | 22.8 | 1.57-1.67 (m) |
| $CH_2$(17) | 31.1 | 1.31-1.38 (m) |
| $CH_2$(18) | 22.4 | 1.31-1.38 (m) |
| Me(19) | 13.9 | 0.87 (t, J = 7.6) | rel-(1S,7aR,3aR)-1-Hexanoyl-5,13dimethyl-6-(2-oxopentyl)7a,7-dihydrobenzofuran-2,4-dione (Compound 1). Colorless oil. $[α]_D^{25}$=+494.4 (c=0.4, $CHCl_3$). UV (MeOH): 253 (4.05). IR (Neat): 1779 (γ-lactone), 1697 (conjugated C=O), 1644 (olefinic). $^1$H- and $^{13}$C-NMR see Table 1. ESI-MS: 362 ($[M+Na]^+$). HR-ESI-MS: 362.2097 ($[M+Na]^+$, $C_{21}H_{30}NaO_5^+$; calcd. 362.2093).

Structure Elucidation of Compound 1

Figure 2:
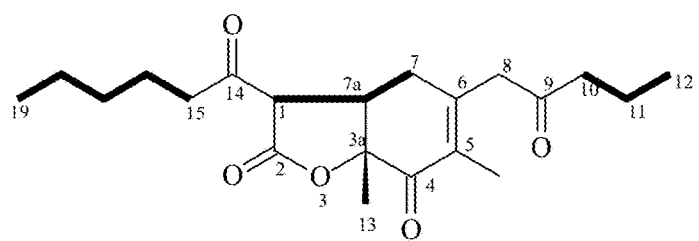
FIG. 2 shows significant COSY (-), NOESY (↔) and HMBC (→) correlations of Compound 1.
Figure 2:
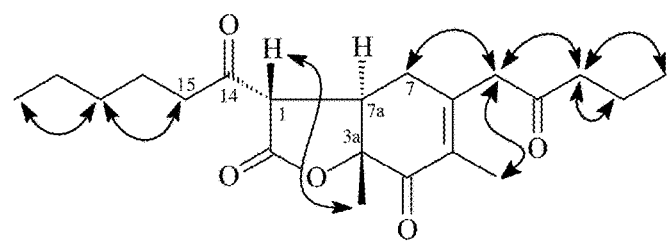
Figure 2:
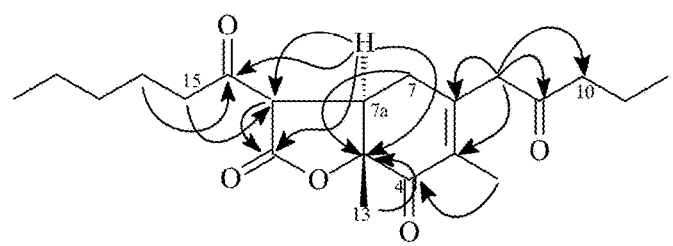

Compound 1 was obtained as colorless oil. The molecular formula was determined as $C_{21}H_{30}O_5$ (seven degrees of unsaturation) by HR-ESI-MS (m/z 362.2093, ($[M+Na]^+$, $C_{21}H_{30}NaO_5^+$; calcd. 362.2093)), which was in agreement with the $^1$H- and $^{13}$C-NMR data (see *Exper. Part*). The UV spectrum absorption $λ_{max}$ (MeOH) at 253 nm, and a strong IR absorption at 1697 $cm^{-1}$, as well as the observation of the featuring carbon resonances [δ(C) 193.4 (qC, C(4)), 131.9 (qC, C(6)), and 148.2 (qC, C(5))] in the $^{13}$C-NMR spectrum (Table 1) revealed the presence of an α,β-unsaturated carbonyl functionality (cyclohex-2-enone moiety) in Compound 1. Its IR spectrum showed absorption bands for γ-lactone (1779 cm$^{-1}$), conjugated C=O (1697 cm$^{-1}$), and one olefinic (1644 cm$^{-1}$) functionalities. The $^1$H- and $^{13}$C-NMR (Table 1), HMBC (FIG. 2), COSY (FIG. 2), and NOESY (FIG. 2) determine compound 1 to be rel-(1S,7aR,3aR)-1-hexanoyl-5,13-dimethyl-6-(2-oxopentyl)-7a,7-dihydrobenzofuran-2,4-dione.

Twenty-one C-atom signals (Table 1) corresponding to seven quaternary C-atoms, two CH, eight $CH_2$, and four Me groups were observed in the $^{13}$C-NMR and DEPT spectra. The $^1$H-NMR spectrum of 1 exhibited signals attributed to one allylic Me (δ(H) 1.79 (br. t, J=1.8 Hz, Me-C(5))), signals of α-methylene protons of two ketones (δ(H) 2.47 (t, J=7.6 Hz, $CH_2(15)$)), 2.57 (t, J=7.6 Hz, $CH_2(10)$)), 3.25 (d, J=17.0 Hz, 1 H of $CH_2(8)$), and 3.65 (d, J=17.0 Hz, 1 H of $CH_2(8)$)), four β-methylene protons of two ketones (δ(H) 1.57-1.67 (m, $CH_2(11)$ and $CH_2(16)$)), one methylene protons (δ(H) 2.58 (dd, J=18.0, 4.4 Hz, 1 H of $CH_2(7)$), and 2.99 (dd, J=18.0, 10.8 Hz, 1 H of $CH_2(7)$)), and two terminal Me moieties (δ(H) 0.87 (t, J=7.6 Hz, Me(19)) and 0.94 (t, J=7.6 Hz, Me(12)). The $^{13}$C-NMR and DEPT spectra exhibited the presence of four C=O carbonyl functions including one α,β-unsaturated C=O group (δ(C) 193.4 (C(4))), one lactone C=O group (δ(C) 169.5 (C(2))), and two saturated ketone groups (δ(C) 202.4 (C(14)) and 205.9 (C(9))), one C=C bond (δ(C) 131.9 (C(6)) and 148.2 (C(5))), and one oxymethyl group (δ(C) 17.2 (C(13))). Since five out of seven unsaturation equivalents were accounted for by the abovementioned $^{13}$C-NMR data, 1 was inferred to have two rings (ring A as a six-membered and ring B as a five-membered ring). In addition, rings A and B were further determined as a cyclohex-2-enone backbone combined with one γ-lactone ring by the following HMBC and COSY analyses.

From the $^1$H-$^1$H COSY spectrum (H—C(10) (δ(H) 2.57)/H—C(11) (δ(H) 1.57-1.67), H—C(11)/H—C(12) (δ(H) 0.94); H—C(15) (δ(H) 2.47)/H—C(16) (δ(H) 1.57-1.67), H—C(16)/H—C(17) (δ(H) 1.31-1.38), H—C(17)/H—C(18) (δ(H) 1.31-1.38), H—C(18)/H—C(19) (δ(H) 0.87)) together with HMBC correlations between the C=O group (δ(C) 205.9 (C(9))) and $CH_2(8)$ (δ(H) 3.25/3.65), $CH_2(10)$ (δ(H) 2.57), and $CH_2(11)$ (δ(H) 1.57-1.67), and between the C=O group (δ(C) 202.4 (C(14))) and H—C(1) (δ(H) 3.64), H—C(7a) (δ(H) 3.16), $CH_2(15)$ (δ(H) 2.47), and $CH_2(16)$ (δ(H) 1.57-1.67) established the presence of 2-oxopentyl ($C_3H_7COCH_2$—, from $CH_2(8)$ to Me-C(12)) and hexanoyl moieties ($C_5H_{11}CO$—, from C(14) to Me-C(19), respectively.

Further confirmation by $^1$H-$^1$H COSY plot (H—C(1) (δ(H) 3.64)/H—C(7a) (δ(H) 3.16)/$CH_2(7)$ (δ(H) 2.58/2.99)) and by the HMBC correlations of Me(13) and C(3a), C(7a), and C(4); H—C(7a)/C(3a) and C(2); $CH_2(7)$/C(3a) and C(7a); Me(5)/C(4), C(5), and C(6) determined the skeleton of Compound 1 to be 5,13-dimethyl-7a,7-dihydrobenzofuran-2,4-dione (rings A & B).

HMBC correlations between the H-atom signal at δ(H) 3.25/3.65 ($CH_2(8)$) and the C-atom signals at δ(C) 131.9 (C(6)), and 148.2 (C(5)) established the position of the 2-oxopentyl group at C(6). The HMBC showed correlations between the H-atom at δ(H) 2.47 ($CH_2(15)$) and the C-atom at δ(C) 54.8 (C(1)); and between the H-atom at δ(H) 3.16 (H—C(7a)) and the C-atom at δ(C) 202.4 (C(14)) can verify the connection of the hexanoyl group to the γ-lactone ring at C(1). The other key correlations of HMBC are illustrated in FIG. 1.

Figure 3:
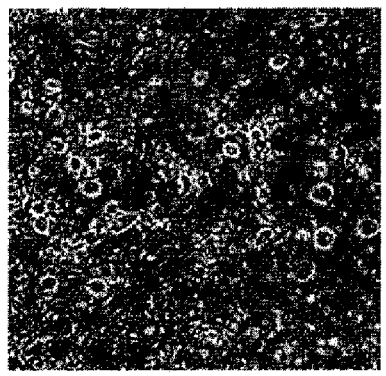
FIG. 3 shows the effects of insulin (A) and Compound 1 (in the concentrations of 2 μg/ml (B), 5 μg/ml (C) and 10 μg/ml (D)) on the differentiation of 3T3-L1 preadipocytes.
Figure 3:
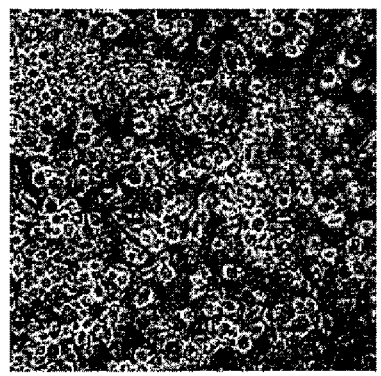
Figure 3:
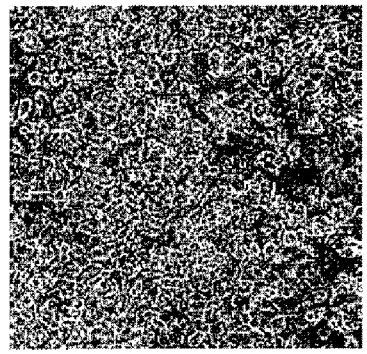
Figure 3:
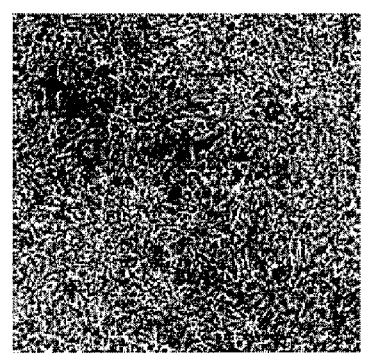
Figure 4:
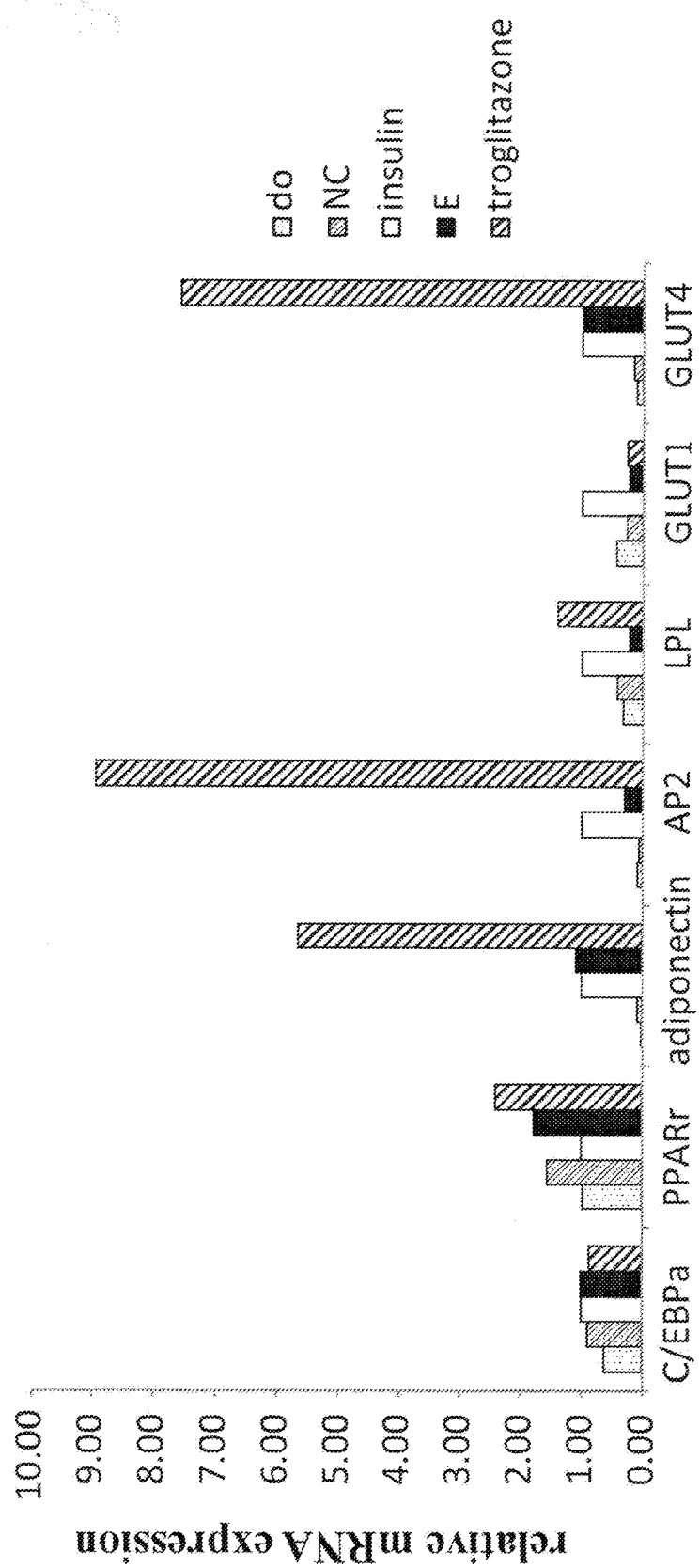
FIG. 4 shows the real-time PCR results of the adipocyte differentiation related gene expressions of the adipocytes treated with Compound 1 on day 4.

The relative configuration of Compound 1 was derived by a NOESY spectrum (FIG. 2) in combination with biogenetic considerations and comparison with similar compound. NOEs for Me-C(13)/H—C(1), Me-C(13)/$H_{ax}$—C(7), and H—C(1)/$H_{ax}$—C(7) indicated that Me-C(13), H—C(1), and $H_{ax}$—C(7) were on the same side of the molecular plane, tentatively assumed as β-orientation. The H—C(7a) was α-oriented which was further confirmed by the NOE H—C(7a)/$H_{eq}$—C(7). Thus, the trans-configuration for H—C(7a) (δ(H) 3.16)/H—C(1) (δ(H) 3.64) was deduced from no NOE correlation between H—C(7a) and H—C(1) and coupling constant $^3$J value 12.8 Hz between H—C(1)/H—C(7a) and H—C(7a)/$H_{ax}$—C(7). The H—C(7a)/$CH_2(15)$ and $CH_2(7)$/$CH_2(8)$ NOESY cross-peaks report on a preferred conformation of the hexanoyl and 2-oxopentyl groups around the C(1)-C(14) and C(6)-C(8) bonds, respectively. On the other hand, the NOE cross peaks $CH_2(8)$/Me-C(5), $CH_2(10)$/$CH_2(11)$, and $CH_2(10)$/Me-C(12) were also observed in FIG. 2. Based on the information from the $^1$H NMR, COSY, and NOESY spectra, a computer-generated 3D structure was obtained by using the abovementioned molecular modeling program with MM2 force-field calculations for energy minimization (FIG. 3). The calculated distances between H—C(1)/Me-C(13) (2.396 Å) are less than 4.00 Å, and between H—C(1)/H—C(7a) (4.486 Å) and Me-C(13)/H—C(7a) (4.320 Å) are more than 4.00 Å; this is consistent with the well-defined NOESY (FIG. 2) observed for each of the proton pairs. Consequently, the relative configuration of C(1), C(7a), and C(3a), was assigned as rel-(1S,7aR,3aR) (FIG. 3).

Example 5

Compound 1 Enhanced Adipocyte Differentiation in 3T3-L1 Cells

Preparation of 3T3-L1 Preadipocytes

Preadipocytes were prepared according to the method described by Wald et al., (2007, "The small molecule harmine is an antidiabetic cell-type-specific regulator of PPARγ expression." *Cell Metabolism*, 5(5): 357-370). Preadipocytes were cultured in DMEM (Dulbecco's Modified Eagle's Medium-high glucose, Sigma D-7777) containing 10% of fetal bovine serum (FBS) and incubated at 37° C. in a 5% $CO_2$ incubator.

Before the differentiation induction experiments, the cells were plated into either 96- or 24-well plates (the concentration of cells in each well was about $2\times10^4$/cm$^2$). The plates were incubated for about two days to allow the cells to proliferate to confluence, and then maintained for another two days. The medium was changed to different differentiation media according to different experiments. The day of switching to differentiation medium was designated as day zero.

Insulin Differentiation Model

The differentiation medium used in insulin differentiation model was DMEM with % FBS comprising 10 µg/ml of insulin. Differentiation media with various concentrations of Compound 1 were added to each well of the 24- or 96-well 3T3-L1 preadipocyte plates (the final concentration of Compound 1 in each well was 2 µg/ml, 5 µg/ml, 10 µg/ml, and 20 µg/ml, respectively). The control group was the culture with only the differentiation medium and no sample. The cultures were incubated at 37° C. in a 5% $CO_2$ incubator for seven days (during the period, the differentiation medium and sample were replaced with fresh ones twice), and then the medium was replaced by DMEM with 10% FBS. The cultures were maintained until day 9 or day 10. The cells of the experiment groups and control groups at day 9 or day 10 were stained with AdipoRed and the concentrations of triglyceride were analyzed.

AdipoRed Staining

The 96-well plates were rinsed with PBS, and 200 μl of PBS and 5 μl of AdipoRed reagent (Lonze Walkersville, Inc., Walkersville, Md., USA, Catalog No. PT-7009) were added to each well. After 10 to 15 minutes, the plates were read with a spectrofluorometer (Infinite M200) set at an excitation wavelength of 485 nm and an emission wavelength of 572 nm. The fluorescent data of the experiment group was divided by the fluorescent data of the control group to obtain a percentage of induction activity.

Measurement of Triglyceride Concentration

The 24-well plates were rinsed with PBS, and the cells were washed off with 0.1 ml of 1% Triton X 100 per well. The cells were then frozen, thawed and centrifuged (10,000 rpm/5 min) and the supernatant was collected. An aliquot of 0.05 ml of the supernatant was analyzed using Triglycerol assay Kit (Audit Diagnostics, Ltd.).

The protein amounts were analyzed using Bio-Rad Dc Protein assay reagent (Bio-Rad). The triglyceride concentration was divided by the protein concentration obtained using Bio-Rad Dc Protein assay to calculate the amount (μg) of triglyceride per μg protein. The triglyceride amounts of the experiment groups were divided by those of the control groups to determine the differentiation induction activity of the samples.

Results

FIGS. 3(A) to 3(D) show the effects of insulin and various concentrations of Compound 1 on the differentiation of 3T3-L1 preadipocytes in insulin differentiation model observed under an inverted microscope. The red color indicates the abundance of triglyceride droplets present in differentiated adipocytes. It was found that the cultures treated with 2 μg/ml (FIG. 3B), 5 μg/ml (FIG. 3C), and 10 μg/ml (FIG. 3D) Compound 1, respectively, contained more triglyceride droplets than the control culture (FIG. 3A), and the quantity of triglyceride droplets increased with dose of Compound 1 indicating that Compound 1 can significantly promote the differentiation of 3T3-L1 preadipocytes.

The extent of enhancement of Compound 1 and troglitazone on 3T3-L1 differentiation were shown in Table 2.

TABLE 2

Extent of Enhancement of Compound 1 on 3T3-L1 Differentiation in Insulin Models

|  | Conc. (μg/ml) | Oil Red assay (% of control) |
| --- | --- | --- |
| MnE | 2 | 127 ± 4 |
|  | 5 | 140 ± 5 |
|  | 10 | 148 ± 8 |

It is found that Compound 1 can promote the differentiation of 3T3-L1 preadipocytes in insulin model.

Example 6

Compound 1 Demonstrating PPARγ Binding Activity 10, 20, 40, 80 and 160 μg/ml of Compound 1 were tested in the ligand binding assay conducted following the manuals described in LanthaScreen TR-FRET PPAR Competitive Binding Assay kits (Invitrogen New York, N.Y. Catalog no. PV4894). In a 96-well microtiter plate, the reagents were pipetted into each well in the following order: 20 μL 2× Test Compound, 10 μL 4× Fluormone™ Pan-PPAR Green and 10 μL 4× PPARγ-LBD/Tb-anti-GST Ab in a total assay volume of 40 μl/well. The reagents were gently mixed by placing the microtiter plate on an orbital plate shaker for 30 seconds. The samples were incubated at room temperature (20-25° C.) for 2 hours in the dark allowing the binding of the samples to reach equilibrium. The fluorescent emission signal of each well was measured at 495 nm and 520 nm with an Absorbance Microplate Reader (Spectra Max M5 from Molecular Devices LLC).

The results show that Compound 1 can bind PPARγ with an $IC_{50}$ value of 68±21 μg/mL.

Example 7

Compound 1 Regulating the mRNA Expression of Upstream Genes Regulating Adipocyte Differentiation in 3T3-L1 Cells The upstream genes that regulate adipocyte differentiation have been previously reported (F. M. Gregoire, C. M. Smas and H. S. Sul, *Understanding adipocyte differentiation. Physiological Reviews*, 783 (1998), pp. 783-809.) Among them, aP2, LPL, PPARγ, adiponectin, GLUT4, GLUT1, and C/EBPα were assayed to monitor the regulation of 3T3-L1 preadipocyte differentiation. The housekeeping genes of β-actin and Glyceraldehyde 3-phosphate dehydrogenase (GADPH) were used as control. "do" represents the conditions of the 3T3-L1 preadipocytes before adding inducing agents. In the "NC" groups, the 3T3-L1 preadipocytes were not treated with any inducing agent. Both "do" and "NC" groups were the control groups. In the groups of "insulin," "E," and "troglitazone," the 3T3-L1 preadipocytes were induced with insulin, Compound 1 and insulin, and troglitazone, respectively.

After culturing the 3T3-L1 cells for 9 days, insulin, Compound 1 and insulin, and troglitazone were added to the medium. The cells were further cultivated, and the samples were collected on day 4 (early adipocyte differentiation stage), day 7 (middle stage) and day 9 (late stage) for the following assays.

RNA Preparation and Quantitative Real-time PCR

Total RNA was extracted from 3T3-L1 cells using TRIZOL reagent according to the manufacturer's instructions (GIBCO 15596-026; Molecular Research Center, Inc). 4 μg of total RNA from each sample were reverse-transcribed to cDNA according to the protocol of the reverse transcript system [RevertAid H Minus First Strand cDNA Synthesis Kit (Fementas K1632)] with the oligo (dT)18 primers. A TaqMan One-Step RT-PCR Master Mix reagent kit and inventory primer and probes (Applied Biosystems, Foster, Calif.) were applied for the quantitative real-time PCR followed by a TaqMan gene expression assay.

The sequences aP2 (Mm00445878_ml), LPL (Mm00434770_ml), PPARγ (Mm01184322_ml), adiponectin (Mm00456425_ml), GLUT4 (Mm01245502_ml), GLUT1 (Mm01192270_ml), C/EBPα (Mm01265914_sl), C/EBPδ (Mm00786711_sl), β-actin (Mm01205647_gl) and GADPH (Mm99999915_gl) were amplified in the PCR. Levels of mRNAs for housekeeping genes (β-actin and GADPH) were also measured by the real-time PCR. After cDNA synthesis, the quantitative real-time PCR was performed with the ABI Prism 7300 instrument (Applied Biosystems, Foster City, Calif., USA) according to the manufacturer's protocol. The PCR conditions were 1 cycle of 50°

C. for 2 min, then 95° C. for 10 min, followed by 40 cycles of 95° C. for 15 seconds and 60° C. for 1 min. The quantification was performed in duplicate and the experiments were repeated independently three times.

Figure 5:
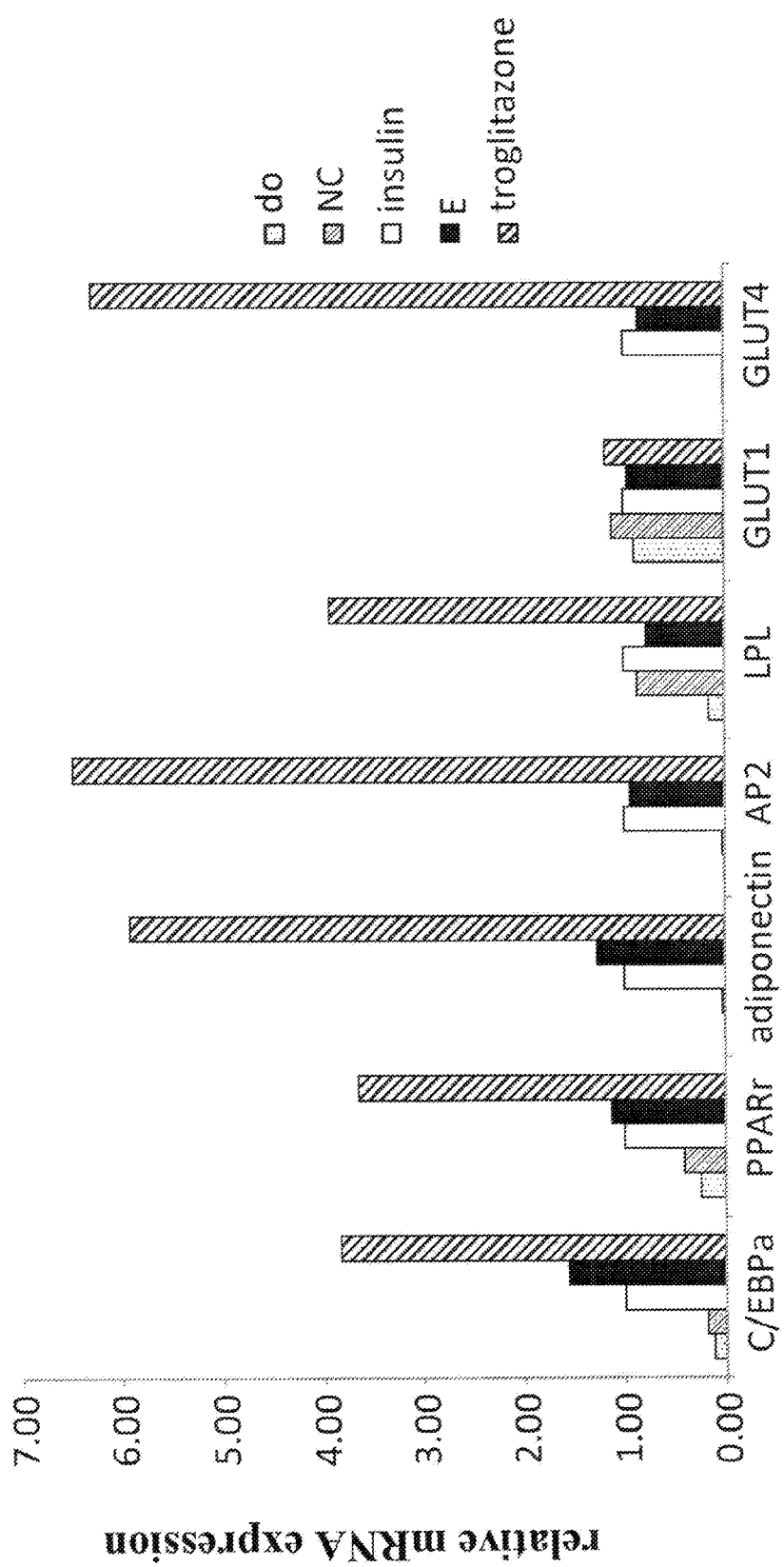
FIG. 5 shows the real-time PCR results of the adipocyte differentiation related gene expressions of the adipocytes treated with Compound 1 on day 7.
Figure 6:
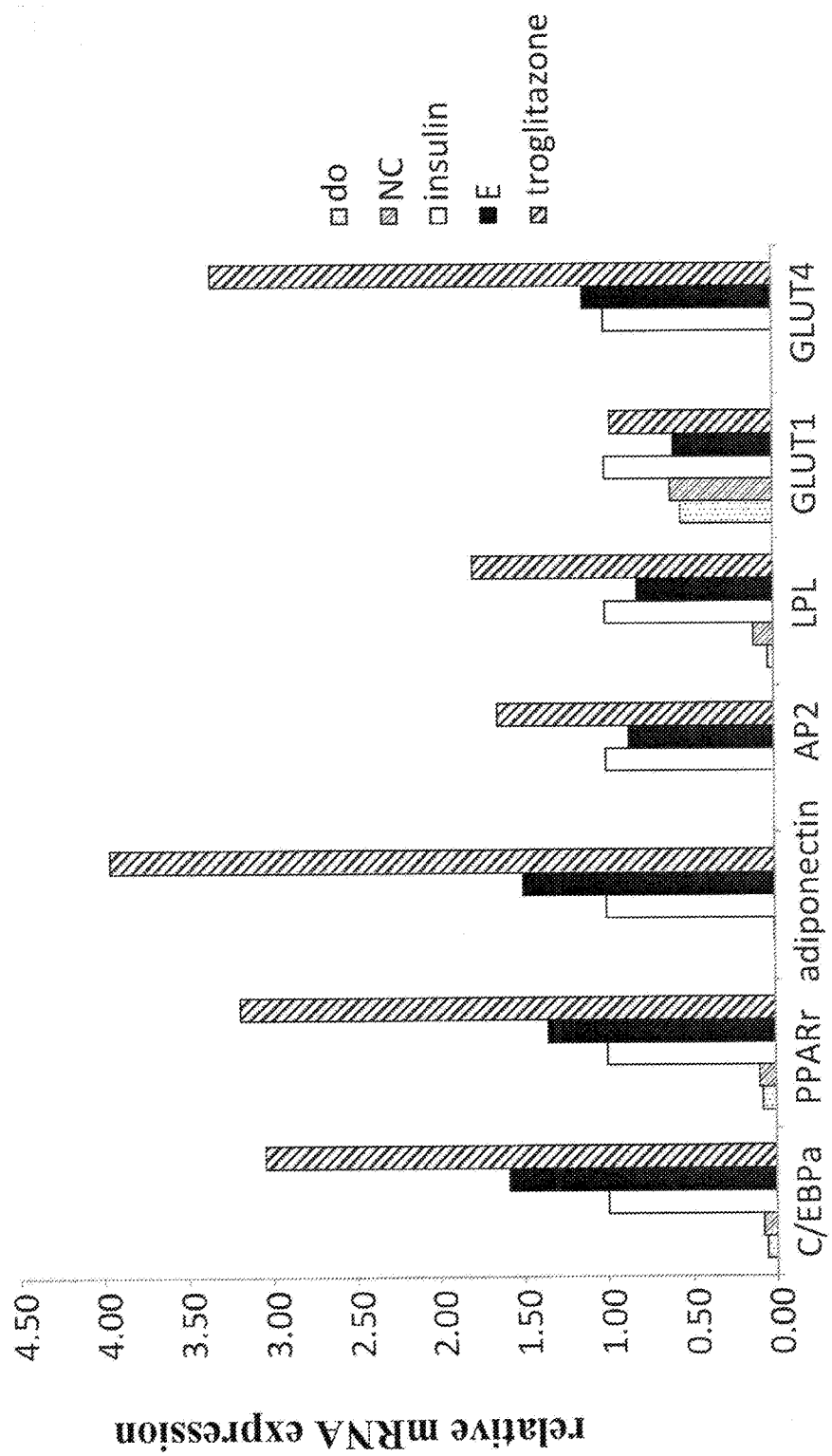
FIG. 6 shows the real-time PCR results of the adipocyte differentiation related gene expressions of the adipocytes treated with Compound 1 on day 9.

FIG. 5 shows that the expressions of C/EBPα, PPARγ and andadiponectin in the E group increase about 50% as compared to the insulin group at the early adipocyte differentiation stage (day 4), but the expression of GluT1 is 0.6 fold of the insulin group. FIG. 6 shows that at the middle adipocyte differentiation stage (day 7), the expression of PPARγ is elevated slightly (1.8 fold) in the E group, but the expressions of aP2, LPL and GluT1 are dramatically lowered (0.3 fold) as compared to the insulin group. FIG. 7 shows that at the late adipocyte differentiation stage (day 9), the expression of C/EBPα, PPARγ and adiponectin in the E group is elevated slightly (1.59, 1.35, 1.49 folds, respectively) as compared to the insulin group, but the expression of GluT1 is 0.6 fold of the insulin control.

The results show that Compound 1 can stimulate the expressions of PPARγ and C/EBPα at the early, middle and late adipocyte differentiation stages, but has little effect on the expression of aP2, LPL, adiponectin, GLUT4, and GLUT1. This demonstrates that Compound 1 enhances the differentiation of preadipocytes to adipocytes through the PPARγ/C/EBPα pathway (Evan D. Rosen, Chung-Hsin Hsu, Xinzhong Wang, Shuichi Sakai, Mason W. Freeman, Frank J. Gonzalez, and Bruce M. Spiegelman. (2002) C/EBPα induces adipogenesis through PPARγ: a unified pathway. *Genes Dev.* 16(1): 22-26).

While the present invention has been described in conjunction with the specific embodiments set forth above, many alternatives thereto and modifications and variations thereof will be apparent to those of ordinary skill in the art. All such alternatives, modifications and variations are regarded as falling within the scope of the present invention.

What is claimed is:

1. A method for preventing and/or treating a disease or disorder related to insulin resistance in a subject, which comprises administering to said subject a composition consisting of an effective amount of rel-(1S,7aR,3aR)-1-hexanoyl-5,13-dimethyl-6-(2-oxopentyl)-7a,7-dihydrobenzofuran-2,4-dione or a pharmaceutically acceptable salt thereof and a pharmaceutically acceptable carrier or excipient.

2. A method of increasing the activity of PPARγ and/or C/EBPα in a subject in need thereof, which comprises administering to said subject a composition consisting of an effective amount of rel-(1S,7aR,3aR)-1-hexanoyl-5,13-dimethyl-6-(2-oxopentyl)-7a,7-dihydrobenzofuran-2,4-dione or a pharmaceutically acceptable salt thereof and a pharmaceutically acceptable carrier or excipient.

3. A method of lowering blood glucose in a subject, which comprises administering to said subject a composition consisting of an effective amount of rel-(1S, 7aR,3aR)-1-hexanoyl-5,13-dimethyl-6-(2-oxopentyl)-7a,7-dihydrobenzofuran-2,4-dione or a pharmaceutically acceptable salt thereof and a pharmaceutically acceptable carrier or excipient.

4. A method of preventing and/or treating metabolic syndrome or its complication in a subject, which comprises administering to said subject a composition consisting of an effective amount of rel-(1S,7aR,3aR)-1-hexanoyl-5,13-dimethyl-6-(2-oxopentyl)-7a,7-dihydrobenzofuran-2,4-dione or a pharmaceutically acceptable salt thereof and a pharmaceutically acceptable carrier or excipient.

5. The method of claim 4, wherein the metabolic syndrome or its complication is selected from the group consisting of abdominal obesity, atherogenic dyslipidemia, elevated blood pressure, insulin resistance or glucose intolerance, type 2 diabetes and cardiovascular disease.

6. The method of claim 5, wherein a second therapeutic agent for preventing or treating metabolic syndrome or its complication is administered to the subject.

7. The method of claim 6, wherein the second therapeutic agent is selected from the group consisting of statins, fibrates, nicotinic acid; diuretics, angiotensin-converting enzyme (ACE) inhibitors; metformin, insulin, sulfonylurea (SU), biguanide, α-glucosidase inhibitors and thiazolidinediones (TZDs).

\* \* \* \* \*